United States Patent
Weber et al.

Patent Number: 5,073,671
Date of Patent: Dec. 17, 1991

[54] 1-(BENZYL OR PYRIDYLMETHYL)-4 OR 5-AMINOMETHYL-PYRROLIDIN-2-ONES

[75] Inventors: Karl-Heinz Weber, Gau-Algesheim; Gerhard Walther, Bingen/Rhein; Claus Schneider, Ingelheim/Rhein; Dieter Hinzen, Bingen/Rhein; Franz J. Kuhn, Gau-Algesheim; Erich Lehr, Waldalgesheim, all of Fed. Rep. of Germany

[73] Assignee: Boehringer Ingelheim KG, Ingelheim am Rhein, Fed. Rep. of Germany

[21] Appl. No.: 632,351

[22] Filed: Dec. 21, 1990

Related U.S. Application Data

[60] Division of Ser. No. 350,597, May 11, 1989, Pat. No. 4,996,224, which is a continuation of Ser. No. 199,291, May 26, 1988, Pat. No. 4,833,140, which is a division of Ser. No. 878,828, Jun. 26, 1986, Pat. No. 4,767,759, which is a continuation-in-part of Ser. No. 657,219, Oct. 3, 1984, abandoned.

[30] Foreign Application Priority Data

Oct. 4, 1983 [DE] Fed. Rep. of Germany ....... 3336024

[51] Int. Cl.$^5$ .................. C07D 401/06; C07D 247/02
[52] U.S. Cl. ...................................... 548/348; 546/278
[58] Field of Search .......................... 548/348; 546/278

Primary Examiner—David B. Springer
Attorney, Agent, or Firm—Walter G. Weissenberger

[57] ABSTRACT

Compounds of the formula

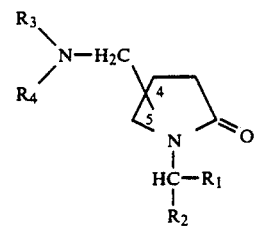

wherein $R_1$ is hydrogen or alkyl of 1 to 4 carbon atoms;
$R_2$ is 2-, 3- or 4-pyridyl, phenyl or mono- or di-substituted phenyl, where the substituents are each individually alkoxy of 1 to 2 carbon atoms, fluorine, chlorine, bromine, trifluoromethyl, alkyl or 1 to 4 carbon atoms, hydroxyl or nitro; and
$R_3$ and $R_4$ are each independently hydrogen or alkyl of 1 to 4 carbon atoms; or
$R_3$ and $R_4$, together with each other and the nitrogen atom to which they are attached, form an unsubstituted or methyl-substituted, saturated 5- or 6-membered heterocycle which may contain an additional oxygen or nitrogen heteroatom, or form an imidazole ring;

where the aminomethyl substituent is attached to the 4- or 5-position or the pyrrolidine ring, and non-toxic, pharmacologically acceptable acid addition salts thereof. The compounds as well as the salts are useful as nootropics and antihypoxics.

1 Claim, No Drawings

1-(BENZYL OR PYRIDYLMETHYL)-4 OR 5-AMINOMETHYL-PYRROLIDIN-2-ONES

This is a divisional application of application Ser. No. 350,597, filed May 11, 1989, now U.S. Pat. No. 4,996,224; which is a continuation of Ser. No. 199,291, filed May 26, 1988, U.S. Pat. No. 4,833,140 which is a divisional of Ser. No. 878,828, filed June 26, 1986 U.S. Pat. No. 4,767,759, which is a continuation-in-part of Ser. No. 657,219, filed Oct. 3, 1984, abandoned.

This invention relates to novel 1-benzyl-4 or 5-aminomethyl-pyrrolidin-2-ones and non-toxic acid addition salts thereof, to methods of preparing these compounds, to pharmaceutical compositions containing them as active ingredients, and to a method of using them as nootropics and antihypoxics.

THE PRIOR ART

Japanese patent application No. 78 44 559 (JP-A-78 44 559) discloses, inter alia, N-[(S)-α-methylbenzyl]-6-oxo-2-(S)-pyrrolidyl-methylamine of the formula

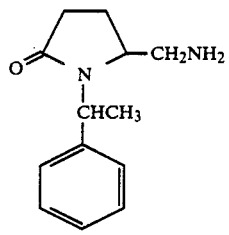

as an intermediate product and does not ascribe any pharmacological properties thereto.

Structurally related nootropics, such as 1-carbamoyl-methyl-pyrrolidin-2-one (piracetam), 1-(p-methoxybenzoyl)pyrrolidin-2-one aniracetam) and 1-carbamoyl-methyl-4-hydroxypyrrolidin-2-one (oxiracetam) are disclosed in the literature; see B. J. R. Nicolaus, Drug Development Res. 2, 464 (1982, and P. L. Paytasch, J.Amer.Chem.Soc. 72, 1415 (1950).

THE INVENTION

More particularly, the present invention relates to a novel class of compounds represented by the formula

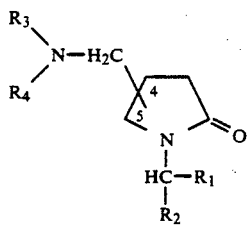

wherein $R_1$ is hydrogen or alkyl of 1 to 4 carbon atoms;

$R_2$ is 2-, 3- or 4-pyridyl, phenyl or mono- or di-substituted phenyl, where the substituents are each individually alkoxy of 1 to 2 carbon atoms, fluorine, chlorine, bromine, trifluoromethyl, alkyl of 1 to 4 carbon atoms, hydroxyl or nitro; and $R_3$ and $R_4$, which may be identical to or different from each other, are each independently hydrogen or alkyl of 1 to 4 carbon atoms; or $R_3$ and $R_4$, together with each other and the nitrogen atom to which they are attached, form an unsubstituted or methyl-substituted, saturated 5- or 6-membered heterocycle which may contain an additional oxygen or nitrogen heteroatom, or form an imidazole ring;

where the aminomethyl substituent is attached to the 4- or 5 - position of the pyrrolidine ring, provided, however, that when the aminomethyl substituent is attached to the 5-position of the pyrrolidine ring, $R_1$ is methyl and $R_3$ and $R_4$ are hydrogen, $R_2$ is other than phenyl, and non-toxic, pharmacologically acceptable acid addition salts thereof.

A preferred subgenus thereunder is constituted by those compounds of the formula I where $R_1$ is hydrogen;

$R_2$ is phenyl or o- or p-monosubstituted phenyl, where the substituent is fluorine, chlorine, methyl or methoxy; and $R_3$ and $R_4$ are each independently hydrogen, methyl or ethyl;

and non-toxic, pharmacologically acceptable acid addition salts thereof.

The compounds embraced by formula I are basic and therefore form addition salts with inorganic or organic acids. Examples of non-toxic, pharmacologically acceptable acid addition salts are those formed with hydrohalic acid, sulfuric, phosphoric, aminosulfonic, formic, acetic, propionic, lactic, glycolic, gluconic, maleic, fumaric, succinic, tartaric, benzoic, salicylic, citric, ascorbic, p-toluenesulfonic, oxyethane sulfonic acid or the like.

The compounds embraced by formula I may be prepared by the following methods:

Method A

For the preparation of a compound of the formula I wherein $R_3$ and/or $R_4$ are other than hydrogen, by reacting a 4- or 5-hydroxymethyl-pyrrolidin-2-one of the formula

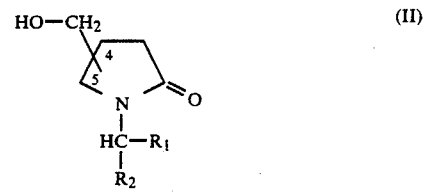

wherein $R_1$ and $R_2$ have the meanings previously defined, with a thionyl halide, a phosphorus halide, a tosyl halide or a mesyl halide to form an intermediate compound of the formula

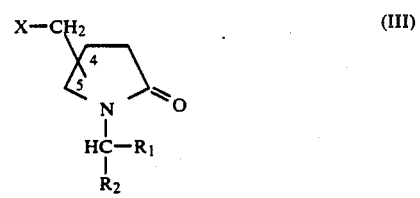

wherein $R_1$ and $R_2$ have the meanings previously defined, and

X is halogen, tosyloxy or mesyloxy, and subsequently reacting said intermediate compound with a primary or secondary amine of the formula

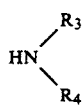 (IV)

wherein $R_3$ and $R_4$ have the meanings previously defined.

A compound of general formula II is converted either with a thionyl or phosphorus halide into the corresponding 4-halomethyl compound or with a tosyl or mesyl halide into the corresponding 4-tosyl or 4-mesyl ester. The reaction is preferably carried out in an inert organic solvent such as chloroform, methylene chloride, tetrahydrofuran or dimethylformamide at temperatures between room temperature and the boiling point of the solvent which is used. In the case of esterification, a tertiary organic base such as triethylamine or pyridine is preferably added. The 4-halomethyl compounds produced as intermediates or the 4-tosyl or 4-mesyl esters may be isolated or may be reacted further in situ. When they are subsequently treated with a primary or secondary amine, the corresponding end products of the formula I are obtained. The reaction may be carried out in tetrahydrofuran, dioxane, acetonitrile or, preferably, in dimethylformamide at a temperature between about 50° and 150° C. the individual reaction conditions depend on the basicity and the boiling point of the amine. The reaction may also be carried out without the use of a solvent in an excess of the amine. In the case of low-boiling-point amines, the reaction must be carried out in an autoclave under certain circumstances.

The end products of the formula I with a free amino group are preferably synthesized by reacting a compound of the formula III with phthalimide or an alkali metal salt of phthalimide, and cleaving the 4-phthalimidomethyl compound thus obtained with hydrazine.

The reaction with phthalimide is carried out in an inert organic solvent such as acetonitrile or an alcohol, or preferably in dimethylformamide, at elevated temperatures up to the boiling point of the reaction mixture. The 4-phtalimidomethyl compound may be isolated or reacted further in situ; the phtalimide group may be split off with hydrazine. For this purpose, alcohols, tetrahydrofuran, dioxane, dimethylformamide or mixtures of alcohols and dimethylformamide may be used as solvents. Frequently, the reaction starts even at room temperature; if desired, a higher temperature may be used in order to speed up the reaction.

Method B

Another method of preparing the nor compound comprises hydrogenating a compound of the formula

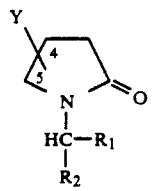 (V)

wherein $R_1$ and $R_2$ have the meanings previously defined, and

Y is $-CH_2N_3$ or $-CN$.

The hydrogenation is preferably carried out with Raney nickel in methanol or with palladium in methanol/water, and possibly with the addition of ammonia in the case of the hydrogenation of the nitrile.

An azide of the formula V ($Y=-CH_2N_3$) is obtained by reacting a compound of the formula III wherein X is halogen, or mesyl, with sodium azide in an inert organic solvent, for instance an alcohol or an ether such as tetrahydrofuran or dioxane.

A nitrile of the formula V ($Y=-CN$) may be prepared, for example, by reacting a solution of a carboxylic acid of the formula VI

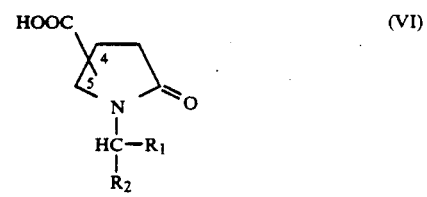 (VI)

wherein $R_1$ and $R_2$ have the meanings previously defined, in acetonitrile with chlorosulfonyl isocyanate and subsequently with triethylamine, or by dehydration of the corresponding carboxylic acid amide with $POCl_3$, for example (cf. H. Vorbrüggen, Tetrahedron Letters 1968, pages 1631-1634).

The novel compounds of the formula I have a center of asymmetry and therefore occur as racemates. These racemates may be converted in the usual way, for instance by salt formation with optically active acids, into the corresponding diastereoisomers, which can then be converted into the optically active end products.

If desired, the alcohols of the formula II may be converted by ester formation with optically active acids into the corresponding mixtures of diastereoisomers which can then be resolved into the individual diastereoisomers by conventional methods, for instance by column chromatography or fractional crystallization. After hydrolysis of these esters, the enantiomeric alcohols are obtained from which the corresponding amines are prepared by method A or B.

Starting from the enantiomeric nor compounds, the corresponding optically pure diethyl compounds may .be obtained by reductive alkylation, for example with acetaldehyde/$H_2$/catalyst, or the corresponding optically pure dimethyl compounds may be obtained with formaldehyde/formic acid.

The starting materials for methods A and B described above are known or may be obtained by known methods. Thus, a pyrrolidinone carboxylic acid of the formula VI is prepared by reacting equimolar quantities of itaconic acid and a corresponding amine. The starting compounds of the formula II can be obtained from the acid via the ester by selective reduction with a complex alkali metal borohydride (cf. German Offenlegungsschrift No. 3,326,724).

In the case of the 5-aminoalkyl compounds, the commercially available 5-pyrrolidinone-carboxylic acids may be used as starting materials; these are esterified, alkylated at the nitrogen with an optionally substituted benzyl halide, and reacted further as described above.

The following end products of the formula I may be obtained, for example, using the methods described above, possibly in the form of their acid addition salts and possibly in the form of the pure enantiomers:

1-Benzyl-4-aminomethyl-pyrrolidin-2-one,
1-(4-Methoxybenzyl)-4-aminomethyl-pyrrolidin-2-one,
1-(3,4-Dimethoxybenzyl)-4-aminomethyl-pyrrolidin-2-one,
1-(4-Methylbenzyl)-4-aminomethyl-pyrrolidin-2-one,
1-(4-Fluorobenzyl)-4-aminomethyl-pyrrolidin-2-one.
1-(4-Chlorobenzyl)-4-aminomethyl-pyrrolidin-2-one,
1-(3-Trifluoromethylbenzyl)-4-aminomethyl-pyrrolidin-2-one,
1-(4-Pyridylmethyl)-4-aminomethyl-pyrrolidin-2-one,
1-(o-Methylbenzyl)-4-aminomethyl-pyrrolidin-2-one,
1-Benzyl-4-piperidinomethyl-pyrrolidin-2-one,
1(4-Fluorobenzyl)-4-morpholino-methyl-pyrrolidin-2-one,
1-Benzyl-4-(N-methylpiperazino)-methyl-pyrrolidin-2-one,
1-Benzyl-4-imidazol-1-yl-methyl-pyrrolidin-2-one,
1-Benzyl-4-methylaminomethyl-pyrrolidin-2-one,
1-(p-Fluorobenzyl)-4-dimethylaminomethyl-pyrrolidin-2-one,
1-Benzyl-4-diethylaminomethyl-pyrrolidin-2-one,
1-(4-Nitrobenzyl)-4-aminomethyl-pyrrolidin-2-one,
1-(4-Hydroxybenzyl)-4-aminomethyl-pyrrolidin-2-one,
1-(o-Chlorobenzyl)-4-aminomethyl-pyrrolidin-2-one,
1-(o-Chlorobenzyl)-4-diethylaminomethyl-pyrrolidin-2-one,
1-Benzyl-4-isopropylaminomethyl-pyrrolidin-2-one,
1-(p-Methylbenzyl)-4-diethylaminomethyl-pyrrolidin-2-one,
1-Benzyl-5-dimethylaminomethyl-pyrrolidin-2-one,
1-Benzyl-5-diethylaminomethyl-pyrrolidin-2-one,
1-Benzyl-5-morpholinomethyl-pyrrolidin-2-one,
1.Benzyl-5-(4-methylpiperazino)-methyl-pyrrolidin-2-one,
1-Benzyl-5-pyrrolidinomethyl-pyrrolidin-2-one,
1-(4-Methylbenzyl)-5-dimethylaminomethyl-pyrrolidin-2-one,
1-(4-Methylbenzyl)-5-diethylaminomethyl-pyrrolidin-2-one,
1-(p-Chlorobenzyl)-5-dimethylaminomethyl-pyrrolidin-2-one,
1-(p-Chlorobenzyl)-5-diethylaminomethyl-pyrrolidin-2-one,
1-(3,4-Dichlorobenzyl)-5-dimethylaminomethyl-pyrrolidin-2-one,
1-(3,4-Dichlorobenzyl)-5-diethylaminomethyl-pyrrolidin-2-one,
1-(p-Methoxybenzyl)-5-dimethylaminomethyl-pyrrolidin-2-one,
1-(p-Methoxybenzyl)-5-diethylaminomethyl-pyrrolidin-2-one,
1-Benzyl-5-aminomethyl-pyrrolidin-2-one.

The following examples illustrate the present invention and will enable others skilled in the art to understand it more completely. It should be understood, however, that the invention is not limited solely to the particular examples given below.

EXAMPLE 1

1-Benzyl-4-aminomethyl-pyrrolidin-2-one

A solution of 54 g (0.16 mol) of 4-phthalimidomethyl-1-benzyl-pyrrolidin-2-one in 1.3 liters of ethyl alcohol was stirred, after the addition of 32 g of hydrazine hydrate, for 4 hours at room temperature. The precipitate (phthalic acid hydrazide) was suction-filtered off, and the filtrate was evaporated. 500 ml of methylene chloride was added to the residue, and the mixture was extracted three times with 100 ml of water. The organic phase was dried and evaporated. The residue was dissolved in 500 ml of methanol, and 20 g (0.17 mol) of solid fumaric acid were added in batches to the boiling mixture while stirring. Upon cooling, colorless crystals precipitated which were suction-filtered off and then washed with methanol and ether. Yield 20-25 g (48-60% of theory), m.p. 190°-192° C. The compound contained ½ mol of fumaric acid.

The starting material was obtained as follows:

(a) 94 g (0.46 mol) of 1-benzyl-4-hydroxymethylpyrrolidin-2-one were stirred with 700 ml of methylene chloride and 40 ml (0.54 mol) of thionylchloride for 25 hours while refluxing, and the reaction mixture was then neutralized with dilute ammonia while cooling. After separation, drying and evaporation, 85-90 g of a dark oil were left behind, which is used directly for further reaction.

(b) A mixture of 43.5 g (0.195 mol) of crude 1-benzyl-4-chloromethyl-pyrrolidin-2-one, 36 g (0.195 mol) of phthalimide potassium and 700 ml of dimethylformamide was refluxed for two hours. The reaction mixture was then evaporated in vacuo, and the residue was taken up in methylene chloride. The solution was extracted several times with water, the organic phase was dried, and after chromatography on $SiO_2$ 45 g (70% of theory) of the phthalimido compound were obtained, m.p. 108-109° C.

EXAMPLE 2

1-Benzyl-4-aminomethyl-pyrrolidin-2-one (a) 58 g (0.29 mol) of 1-benzyl-4-cyano-pyrrolidin-2-one were dissolved in methanol and catalytically hydrogenated with the addition of liquid ammonia over Raney nickel. After evaporation of the reaction solution the mixture was dissolved in methanol, the residual catalyst was filtered off, and after the filtrate had been heated to about 50° C. it was mixed with 17 g of fumaric acid. The fumaric acid briefly went into solution upon stirring, and then crystallization of the 1-benzyl-4-aminomethyl-pyrrolidin-2-one fumarate began. Yield: 68 g (91% of theory). M.p. 192°-194° C.

(b) The cyano compound was obtained with a 96% yield in the form of an oil from the corresponding amide. M.p. 162°-166° C. by dehydration with $POCl_3$ in dimethylformamide at about 60° C.

EXAMPLE 3

Racemate cleavage of 1-benzyl-4-aminomethyl-pyrrolidin-2-one (a) 24.0 g (0.117 mol) of 1-benzyl-4.aminomethyl-pyrrolidin-2-one were dissolved in 200 ml of hot methanol, and 17.6 g (0.117 mol) of L(+)-tartaric acid were also dissolved in 200 ml of hot methanol. The two solutions were combined and cooled to room temperature with stirring, whereupon the salt crystallized out. The crystals were suction-filtered off while cold, washed with cold methanol and dried. Yield: 18.0 g of 4-aminomethyl-1-benzyl-pyrrolidin-2-one tartrate. M.p. 204°-206° C. (from methanol), $a_D = +6.3°$ (c = 1.0; water).

(b) In order to convert the tartrate into the base, the tartrate was dissolved in a cold mixture of 20 ml of water and 10 ml of concentrated sodium hydroxide and the solution was extracted three times with methylene chloride. The combined methylene chloride phases were dried over $MgSO_4$, and the solvent was evaporated in vacuo, yielding (−)-4-aminomethyl-1-benzyl-pyrrolidin-2-one, $\alpha_D = -8.4°$ (c=1.0; water).

(c) The mother liquors obtained in the work-up described in (a) were evaporated in vacuo. 38.0 g of the tartrate were obtained, which was taken up in a cold mixture of 140 ml of water and 50 ml of concentrated sodium hydroxide, and the solution was extracted three times with methylene chloride. The combined methylene chloride phases were dried over $MgSO_4$, and the solvent was evaporated in vacuo. 19.3 g of base were obtained, which was converted into the corresponding tartrate with D-(−)-tartaric acid as described in (a). Yield: 19.0 g. M.p. 204°-205° C.

(d) The conversion of the tartrate into the base was carried out as described in (b). 5.7 g of +)-4-aminomethyl-1-benzyl-pyrrolidin-2-one with a rotation $\alpha_D = +8.4°$ (c =1.0; water) were obtained.

EXAMPLE 4

(−)-1-Benzyl-4-dimethylaminomethyl-pyrrolidin-2-one 4.0 g (0.02 mol) of (-)-1-benzyl-4-aminomethyl-pyrrolidin-2-one and 5.4 g of 85% formic acid were mixed with 4.8 ml of formalin solution and stirred overnight at 100° C. (oil bath). Then the excess acid was distilled off in vacuo, the residue was taken up in water, and the solution was made alkaline with concentrated sodium hydroxide and then extracted three times with methylene chloride. The combined methylene chloride phases were washed with water and dried over sodium sulfate, the solvent was evaporated in vacuo, and the residue was filtered through an $SiO_2$ column (eluant: methylene chloride:methanol =97:3). The uniform fraction was evaporated in vacuo. The title compound was obtained with a yield of 3.5 g (in the form of an oil).
$\alpha_D = -7.6°$ (c=1.0; methanol),
$\alpha_D = -16.8°$ (c=1.0; water).

Analogously, 6.1 g of (+)-1-benzyl-4-dimethylaminomethyl-pyrrolidin-2-one were obtained, $\alpha_D = +7.9°$ (c=1.0; methanol), from 5.8 g (0.028 mol) of (+)-1-benzyl-4-aminomethylpyrrolidin-2-one, 7.9 g of 85% formic acid and 7 ml of formalin solution.

EXAMPLE 5

1-Benzyl-4-diethylaminomethyl-pyrrolidin-2-one

A mixture of 14 g (0.06 mol) of crude 1-benzyl-4-chloromethyl-pyrrolidin-2-one, prepared as in Example 1(a), 10 g of diethylamine and 50 ml of dimethylformamide was stirred or shaken for 2 hours at 150° C. in an autoclave. The reaction mixture was evaporated to dryness in vacuo, the residue was taken up in methylene chloride, and the solution was washed first with water and finally the title compound was extracted twice with 25 ml of 2 N HCl. The aqueous phase was separated, made alkaline with sodium hydroxide and the organic base was extracted with methylene chloride. The methylene chloride phase was evaporated, and the residue was distilled in vacuo. Yield: 10 g (61% of theory), $bp_{0.05} = 155°-158°$ C.

EXAMPLE 6

(−)-1-Benzyl-4-diethylaminomethyl-pyrrolidin-2-one

A mixture of 11.5 g (0.056 mol) of (−)-1-benzyl-4-aminomethyl-pyrrolidin-2-one, 130 ml of water, 13 g of acetaldehyde, 5.8 ml of concentrated hydrochloric acid and 6.5 g of 20% palladium-on-charcoal was hydrogenated for 5¼ hours at 5 bar and at 25° C. The reaction mixture was filtered, the filtrate was evaporated, the residue was taken up in 30 ml of water, and the solution was extracted with methylene chloride. The aqueous hydrochloric acid solution was made alkaline and then extracted with methylene chloride. By distillation of the combined extracts in a bulbed tube, 11.2 g (76.4% of theory) of the title compound were obtained, $\alpha_D = -9.4$ (c =1.0; methanol).

Analogously, by hydrogenating a mixture of 8.4 g (0.041 mol) of (+)-1-benzyl-4-aminomethyl-pyrrolidin-2-one, 95 ml of water, 9.5 acetaldehyde, 4.2 ml of concentrated hydrochloric acid and 4.7 g of 20% Pd/C. (+)-1-benzyl-4-diethylaminomethylpyrrolidin-2-one, $\alpha_D = +9.4$ (c =1.0; methanol), was obtained.

EXAMPLE 7

1-(4-Fluoro-benzyl)-4-N-methylpiperazinylmethyl-pyrrolidin-2-one (a) 24 g (0.11 mol) of 1-(4-fluorobenzyl)-4-hydroxymethyl-pyrrolidin-2-one were refluxed with 10 ml (0.14 mol) of thionyl chloride in 200 ml of methylene chloride first for 10 hours and then, after the addition of another 10 ml of thionyl chloride, for 6 hours more. While cooling with ice, the reaction mixture was neutralized with ammonia, and after the organic phase was separated, it was dried and evaporated. 23 g (92% of theory) of a reddish-brown oil remained, which was used without any further purification.

(b) 5 g (0.002 mol) of the above oil were refluxed for 1 to 2 hours with 4.4 g (0.04 mol) of 1-methyl-piperazine in 30 ml of dimethylformamide. The dimethylformamide was then substantially distilled off in vacuo, the residue was taken up in methylene chloride, the solution was washed with water, and the organic phase was dried and evaporated. The residue was chromatographed on $SiO_2$ with methylene chloride/methanol 95:5 as the eluant. The main fraction was evaporated, and the residue (5 g) was dissolved in 30 ml of methanol. 2.8 g of fumaric acid were added to this solution. 5.2 g (48% of theory) of the fumarate of the title compound were precipitated in crystalline form. M.p. 179°-180° C.

EXAMPLE 8

1-(4-Fluorobenzyl)-4-morpholinomethyl-pyrrolidin-2-one (a) A solution of 8.9 g (0.04 mol) of 1-(4-fluorobenzyl)-4-hydroxymethyl-pyrrolidin-2-one in 100 ml of absolute methylene chloride and 4.8 g of pyridine was mixed with 6.9 g (0.06 mol) of methanesulfonic acid chloride. The mixture was refluxed for 2.5 hours and then cooled and extracted with dilute ammonia and water. The organic phase was dried and evaporated. 11 g (93% of theory) of crude ester, m.p. 84°-86° C., were obtained.

(b) 6.7 g (0.023 mol) of the ester obtained in (a) and 2.6 g (0.03 mol) of morpholine were refluxed for 2 hours in 20 ml of dioxane. The solvent was then evaporated in vacuo, the residue was taken up in methylene chloride, and the solution was extracted with 50 ml of 2 N hydrochloric acid. The aqueous extracts were made alkaline with ammonia, and the oily base which separated out was extracted with methylene chloride. The methylene chloride phase was dried and evaporated. The residue (4.2 g) was taken up in 30 ml of methanol, and 1.2 g of fumaric acid were added to the warm methanolic solution. After cooling, the fumarate of the title compound precipitated in crystalline form.

Yield 7 g =57% of theory of colorless crystals, m.p. 175°–176° C.

EXAMPLE 9

1-(4-Fluorobenzyl)-4-aminomethyl-pyrrolidin-2-one (a) 4.0 g (0.013 mol) of the mesyl ester prepared in Example 7 were refluxed for 30 minutes with 2.8 g (0.015 mol) of phthalimide potassium in 5( ml of dimethylformamide. The reaction mixture was evaporated in vacuo, and the residue was taken up in methylene chloride, the solution was washed with water, and the organic phase was dried and again evaporated. The residue was triturated with ether and yielded 3.6 g (78% of theory) of light grey crystals, m.p. 124°–125° C.

(b) 3.5 g (0.1 mol) of the phthalimide compound obtained in (a) were stirred with 5.5 g of hydrazine hydrate in 200 ml of alcohol for 4 hours at room temperature. The mixture was worked up as described in Example 1. 2.5 g (89% of theory) of the fumarate of the title compound, m.p. 214°–215° C., were obtained.

The title compound may also be obtained by dissolving 5 g (16 mmols) of the mesyl ester (see Example 7) in 100 ml of dimethylformamide and, after the addition of 1.3 g of sodium azide, heating the mixture to 100° C. for 2 hours, hydrogenating the oil which is obtained with Raney nickel in methanol, and converting the base into the fumarate as described above. Yield: 4.2 g (90% of theory).

Using procedures analogous to those described in the preceding examples, the compounds of the formula I shown in the following table were also prepared:

TABLE I

| Example No. | R | $R_1$ | $R_2$ | M.p. °C./Bp. °C. |
|---|---|---|---|---|
| 10 | —$NH_2$ | H | 4-methoxyphenyl | Mp. 215–216 (Fumarate) |
| 11 | —$NH_2$ | H | 2,3-dimethoxyphenyl | Mp. 187–189 (Fumarate) |
| 12 | —$NH_2$ | H | 4-methylphenyl | Mp. 225–266 (Fumarate) |
| 13 | —$NH_2$ | H | 4-chlorophenyl | Mp. 189–191 (Fumarate) |
| 14 | —$NH_2$ | H | 3-(trifluoromethyl)phenyl | Mp. 168–169 (Fumarate) |
| 15 | —$NH_2$ | H | pyridin-4-yl | Mp. 179–181 (Fumarate) |
| 16 | —$NH_2$ | —$CH_3$ | 4-methoxyphenyl | Mp. 167–168 (Fumarate) |
| 17 | piperidin-1-yl | H | phenyl | Mp. 58–60 $Bp_{0.05}$ 180 (Base) |

TABLE I-continued

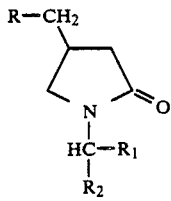

| Example No. | R | $R_1$ | $R_2$ | M.p. °C./Bp. °C. |
|---|---|---|---|---|
| 18 | —N(piperazinyl)N—CH₃ | H | phenyl | Mp. 190–192 (Fumarate) |
| 19 | —N(imidazolyl) | H | phenyl | Mp. $_{0.05}$230 (Base) |
| 20 | —HN—CH₃ | H | phenyl | Bp. $_{0.05}$180 (Base) |
| 21 | —NH₂ | H | 2-Cl-phenyl | Mp. 179–180 (Fumarate) |
| 22 | —N(C₂H₅)₂ | H | 2-Cl-phenyl | Bp. $_{0.05}$156 (Base) |
| 23 | —NH—CH(CH₃)₂ | H | phenyl | Bp. $_{0.05}$175 (Base) |
| 24 | —N(C₂H₅)₂ | H | 4-CH₃-phenyl | Bp. $_{0.05}$175 (Base) |

EXAMPLE 25

1-Benzyl-5-dimethylaminomethyl-pyrrolidin-2-one (a) A solution of 10.26 g (0.05 mol) of 1-benzyl-5-hydroxymethyl-pyrrolidin-2-one (m.p. 76°–77° C.) and 5.6 g (0.055 mol) of triethylamine in 80 ml of methylene chloride was mixed with a solution of 6.3 g (0.055 mol) of methanesulfonic acid chloride in 20 ml of methylene chloride. The reaction mixture was then refluxed for one hour, and after cooling it was extracted with water. The organic phase was dried over anhydrous sodium sulfate and then evaporated in a rotary evaporator. 14.1 g (yellow oil) of crude 1-benzyl-5-hydroxymethyl-pyrrolidine-2-one methanesulfonic acid ester were obtained, which was used in the next reaction step without any further purification.

(b) 8.5 g (0.03 mol) of the mesylate obtained in (a) were heated at 150° C. for 3 hours with a solution of 10 g of dimethylamine in 60 ml of dioxane in an autoclave. After cooling, the reaction mixture was evaporated to dryness in vacuo. The residue was dissolved in 2 N hydrochloric acid, and the solution was extracted with ether. The acidic aqueous phase was made alkaline with concentrated ammonia and then extracted with methylene chloride. The methylene chloride phase was dried and evaporated. The residue (6.5 g) was converted into the acid fumarate of the title compound with an equivalent amount of fumaric acid. Yield: 6.4 g (61% of theory); m.p. 137°–138° C.

Using a procedure analogous to that described in Example 25, the compounds of the formula I shown in the following table were also prepared:

TABLE II

| Example No. | R | $R_1$ | $R_2$ | Mp. °C./Bp. °C. |
|---|---|---|---|---|
| 26 | $-N(C_2H_5)_2$ | H | phenyl | Mp. 163–164 (Hydrochloride) |
| 27 | morpholino | H | phenyl | Mp. 167–169 (Oxalate) |
| 28 | 4-methylpiperazinyl | H | phenyl | Mp. 258 (Dihydrochloride) |
| 29 | pyrrolidinyl | H | phenyl | Mp. 188–190 (Hydrochloride) |
| 30 | $-N(CH_3)_2$ | H | 2-CH$_3$-phenyl | Mp. 163–164 (Fumarate) |
| 31 | $-N(C_2H_5)_2$ | H | 4-CH$_3$-phenyl | Mp. 152–153 (Hydrochloride) |
| 32 | $-N(CH_3)_2$ | H | 4-Cl-phenyl | Mp. 157–158 (Fumarate) |
| 33 | $-N(C_2H_5)_2$ | H | 4-Cl-phenyl | Mp. 149–151 (Hydrochloride) |
| 34 | $-N(CH_3)_2$ | H | 3,4-diCl-phenyl | Mp. 167–168 (Fumarate) |
| 35 | $-N(C_2H_5)_2$ | H | 2,3-diCl-phenyl | Mp. 159–161 (Hydrochloride) |
| 36 | $-N(CH_3)_2$ | H | 4-OCH$_3$-phenyl | Oil (Base) |

TABLE II-continued

R—CH₂—[pyrrolidinone ring with N, C=O]
         |
         HC—R₁
         |
         R₂

| Example No. | R | R₁ | R₂ | Mp. °C./Bp. °C. |
|---|---|---|---|---|
| 37 | —N(C$_2$H$_5$)$_2$ | H | —C$_6$H$_4$—OCH$_3$ | Oil (Base) |

EXAMPLE 38

1-Benzyl-5-aminomethyl-pyrrolidin-2-one 16.4 g (0.07 mol) of 1-benzyl-5-hydroxymethyl-pyrrolidin-2-one methanesulfonic acid ester [see Example 25(a)] were dissolved in 200 ml of dimethylformamide, and the solution was stirred for 90 minutes at 100° C. after the addition of 4.6 g (0.07 mol) of sodium azide. After evaporation of the reaction mixture, taking up the residue in a mixture of water and methylene chloride, and working up of the organic phase, 13.8 g (92% of theory) of an oil were obtained, which was reacted further in its crude form. It was dissolved in 200 ml of methanol, and after the addition of Raney nickel the solution was hydrogenated at 20° C. and 5 bar. After the catalyst had been removed by suction filtration and the filtrate had been evaporated, 11 g (85% of theory) of an oil were obtained which, when dissolved in methanol and after the addition of fumaric acid, yielded the desired hemifumarate of the title compound (m.p. 187°–188° C.).

The compounds of the present invention, that is, those embraced by formula I, as well as 1-(α-methylbenzyl)-5-minomethyl-pyrrolidin-2-one, have useful pharmacodynamic properties. More particularly, they exhibit nootropic activity in warm-blooded animals, that is, they alleviate or cure conditions of impaired functional capacity of the brain.

The above pyrrolidinone derivatives were tested in animal experiments with regard to their activity of curing or alleviating conditions of impaired cerebral performance.

In tolerance tests, which were carried out as a guide, the compounds show no acute toxicity (14 days observation) when administered to mice in doses of up to 2 g/kg (single oral administration). In animal experiments they show excellent effects on spontaneous cognitive performance, such as experimentally impaired learning and memory processes. In tests with a restriction of the short term memory or inhibition of the transition from contents of the short term memory to the long term memory, by the administration of a muscarinic cholinergic antagonist [scopolamine 0.6 mg/kg i.p.; see also Psychopharmacology 78, 104–111 (1982)], the compounds are capable of counteracting or even curing this pharmacologically induced cerebral insufficiency.

The learning capacities of rats in an active avoidance training [J. Pharmacol. Methods, 8, 155–163 (1983)] are improved as is their spontaneous habituation or exploring orientation activity in a new environment.

The pyrrolidinone derivatives were compared in their activity with pyrrolidinones of different structures which are already used as drugs in human medicine (piracetam) or are at present undergoing clinical trials (anirazetam) with regard to cerebral insufficiency or organic brain psychodrome, post-traumatic and alcoholic brain damage, etc.

In tests to determine the survival of animals in a closed chamber (hypoxia tolerance test) through which a gas mixture consisting of 96.5% N$_2$ and 3.5% O$_2$ was passed, the animals pretreated with the pyrrolidinone derivatives had a statistically highly significantly greater survival rate than control animals or animals pre-treated with piracetam. Moreover, the brain-protecting activity of the substances tested by this method was very marked even at a dosage of 50 mg/kg p.o.

The pyrrolidinone derivatives are clearly superior to the above-mentioned pyrrolidinones of different structures, both in their effective dosage and also in the improvement in performance obtained in the animal experiments.

For pharmaceutical purposes the pyrrolidinone derivatives are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 0.7 to 2.8 mg/kg body weight, preferably 1.0 to 2.1 mg/kg body weight.

The compounds may be used either by themselves or in combination with other active substances of the instant invention, possibly together with other pharmacologically active substances, such as other cerebro-activators.

Suitable tablets may be prepared, for example, by mixing the or each active substance with known excipients, for instance with inert diluents such as calcium carbonate, calcium phosphate or lactose, disintegrants such as corn starch or alginic acid, binders such as starch or gelatin, lubricants such as magnesium stearate or talc, and/or agents for obtaining delayed release such as carboxypolymethylene, carboxymethylcellulose, cellulose acetate phthalate or polyvinylacetate. The tablets may also consist of several layers.

Coated tablets may be produced similarly by coating cores produced analogously to the tablets with agents conventionally used in tablet coatings, such as collidone or shellac, gum arabic, talc, titanium oxide or sugar. In order to achieve delayed release or avoid incompatibilities, the core may also consist of several layers. Similarly, the tablet coating may be made up of a number of layers in order to obtain delayed release, and the excipients mentioned for the tablets may be used.

Syrups of the active substances or combinations of active substances according to the invention may additionally contain a sweetener such as saccharin, cyclamate, glycerol or sugar and a flavor-improving agent, for instance a flavoring such as vanillin or orange extract. They may also contain suspension adjuvants or thickeners such as sodium carboxymethylcellulose, wetting agents, for example condensation products of fatty alcohols with ethylene oxide, or preservatives such as p-hydroxybenzoates.

Injection solutions are prepared in the conventional way, for instance by adding preservatives such as p-hydroxybenzoates or stabilizers such as alkali metal salts of ethylene diamine tetraacetic acid, and these solutions are then transferred into injection vials or ampules.

Capsules containing one or more active substances or combinations of active substances may be prepared, for example, by mixing the active substances with inert carriers such as lactose or sorbitol and filling gelatin capsules therewith.

Suitable suppositories may be produced, for example, by mixing with carriers provided for this purpose such as neutral fats or polyethylene glycol or derivatives thereof.

The following examples illustrate a few pharmaceutical compositions comprising a compound of the present invention as an active ingredient and represent the best modes contemplated of using the invention. The parts are parts by weight unless otherwise specified.

EXAMPLE 39

Tablets

The tablet composition is compounded from the following ingredients:

| | |
|---|---|
| 1-Benzyl-4-aminomethyl-pyrrolidin-2-one | 100 parts |
| Lactose (powdered) | 140 parts |
| Cornstarch | 240 parts |
| Polyvinyl pyrrolidone | 15 parts |
| Magnesium stearate | 5 parts |
| | 500 parts |

Preparation

The finely ground active ingredient, lactose and some of the corn starch are mixed together. The mixture is screened, then moistened with a solution of polyvinyl pyrrolidone in water, kneaded, moist-granulated and dried. The granulate, the remaining corn starch and the magnesium stearate are screened and mixed together. The mixture is compressed into 500 mg-tablets of a suitable size and shape, each of which contains 100 mg of the active ingredient.

EXAMPLE 40

Tablets

The tablet compositions is compounded from the following ingredients:

| | |
|---|---|
| 1-(p-Fluorobenzyl)-4-aminomethyl-pyrrolidin-2-one | 80 parts |
| Cornstarch | 190 parts |
| Lactose | 55 parts |
| Microcrystalline cellulose | 35 parts |
| Polyvinyl pyrrolidone | 15 parts |
| Sodium carboxymethyl starch | 23 parts |
| Magnesium stearate | 2 parts |
| | 400 parts |

Preparation

The finely ground active substance, some of the corn starch, lactose, microcrystalline cellulose and polyvinyl pyrrolidone are mixed together, the mixture is screened and processed with the remaining corn starch and water to form a granulate which is dried and screened. The sodium carboxymethyl starch and the magnesium stearate are added, and the mixture is compressed into 400 mg-tablets of a suitable size and shape, each of which contains 80 mg of the active ingredient.

EXAMPLE 41

Injectable solution

The solution is compounded from the following ingredients:

| | |
|---|---|
| 1-(p-Fluorobenzyl)-4-aminomethyl-pyrrolidin-2-one fumarate | 50 parts |
| Sodium chloride | 10 parts |
| Double-distilled water q.s.ad | 1000 parts by vol. |

Preparation

The active ingredient and the sodium-chloride are dissolved in a sufficient quantity of double-distilled water, and the solution is diluted to the desired concentration with the required amount of double-distilled water. The solution is filtered and filled into 1 ml-ampules under aseptic conditions. Finally, the ampules are sterilized and sealed. Each ampule contains 80 mg of the active ingredient.

EXAMPLE 42

Drop solution

The solution is compounded from the following ingredients:

| | |
|---|---|
| 1-(4-Fluorobenzyl)-4-aminomethyl-pyrrolidin-2-one fumarate | 5.0 parts |
| Methyl p-hydroxybenzoate | 0.1 parts |
| Propyl p-hydroxybenzoate | 0.1 parts |
| Demineralized water q.s.ad | 100.0 parts by vol. |

Preparation

The active ingredient and the p-hydroxybenzoates are dissolved in the demineralized water, the solution is filtered, and the filtrate is filled into 100 ml-bottles equipped with a dropping spout. Each bottle contains 5 g of the active ingredient.

Any one of the other compounds embraced by formula I, or 1-($\alpha$-methyl-benzyl)-5-aminomethyl-pyrrolidin-2-one, or a non-toxic, pharmacologically acceptable acid addition salt thereof, may be substituted for the particular active ingredient in Examples 39 through 42. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with, the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

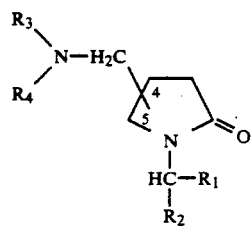

wherein $R_1$ is hydrogen or alkyl of 1 to 4 carbon atoms;

$R_2$ is 2-, 3- or 4-pyridyl, phenyl or mono- or di-substituted phenyl, where the substituents are each individually alkoxy of 1 to 2 carbon atoms, fluorine, chlorine, bromine, trifluoromethyl, alkyl of 1 to 4 carbon atoms, hydroxyl or nitro; and $R_3$ and $R_4$, together with each other and the nitrogen atom to which they are attached, form an an imidazole ring;

where the aminomethyl substituent is attached to the 4- or 5-position of the pyrrolidine ring, or a non-toxic, pharmacologically acceptable acid addition salt thereof.

* * * * *

UNITED STATES PATENT AND TRADEMARK OFFICE
CERTIFICATE OF CORRECTION

PATENT NO. : 5,073,671
DATED : December 17, 1991
INVENTOR(S) : Karl-Heinz Weber et al It is certified that error appears in the above-identified patent and that said Letters Patent is hereby corrected as shown below:

Column 5, line 11, "1-(o" should read --1-(α--.

Column 5, line 33, "1.Benzyl" should read --1-Benzyl--.

Column 6, line 53, "4.amino" should read --4-amino--.

Column 10, Example 12 "266" should read --226--.

Column 15, line 39, "5-mino" should read --5-amino--.

Signed and Sealed this

Tenth Day of August, 1993

Attest:

MICHAEL K. KIRK

Attesting Officer    Acting Commissioner of Patents and Trademarks